(12) United States Patent
Zuñiga Benavides (10) Patent No.: US 9,308,241 B2
(45) Date of Patent: Apr. 12, 2016

(54) FOOD SUPPLEMENT HAVING HIGH IMMUNOLOGICAL VALUE, BASED ON A PROTEIN MATRIX

(76) Inventor: Miguel Alvaro Zuñiga Benavides, Lima (PE)

( * ) Notice: Subject to any disclaimer, the term of this patent is extended or adjusted under 35 U.S.C. 154(b) by 0 days.

(21) Appl. No.: 14/232,446

(22) PCT Filed: Jul. 12, 2012

(86) PCT No.: PCT/PE2012/000002
§ 371 (c)(1),
(2), (4) Date: Jan. 13, 2014

(87) PCT Pub. No.: WO2013/009194
PCT Pub. Date: Jan. 17, 2013

(65) Prior Publication Data
US 2014/0170177 A1    Jun. 19, 2014

(30) Foreign Application Priority Data
Jul. 12, 2011   (PE) .............................. 1340-2011/DIN (51) Int. Cl.
| | |
|---|---|
| *A23L 1/305* | (2006.01) |
| *A61K 38/38* | (2006.01) |
| *A23J 1/08* | (2006.01) |
| *A23J 1/14* | (2006.01) |
| *A23J 1/20* | (2006.01) |
| *A61K 38/16* | (2006.01) |
| *A61K 38/17* | (2006.01) |

(52) U.S. Cl.
CPC . *A61K 38/38* (2013.01); *A23J 1/08* (2013.01); *A23J 1/14* (2013.01); *A23J 1/20* (2013.01); *A23L 1/3053* (2013.01); *A23L 1/3056* (2013.01); *A61K 38/168* (2013.01); *A61K 38/1709* (2013.01)

(58) Field of Classification Search
None
See application file for complete search history.

(56) References Cited

U.S. PATENT DOCUMENTS

| | | | |
|---|---|---|---|
| 4,021,584 | A | 5/1977 | Rankowitz |
| 4,132,809 | A | 1/1979 | Desrosier |
| 5,320,859 | A | 6/1994 | Namdari |
| 2003/0008016 | A1 | 1/2003 | Crum et al. |
| 2003/0044503 | A1 | 3/2003 | Morgan et al. |

FOREIGN PATENT DOCUMENTS

| | | | |
|---|---|---|---|
| CA | 2 552 313 | A1 | 1/2007 |
| CA | 2 520 178 | A1 | 3/2007 |
| EP | 0 391 416 | A1 | 10/1990 |
| EP | 391416 | A1 | 10/1990 |
| EP | 1 803 358 | A1 | 7/2007 |
| ES | 2 155 855 | T3 | 6/2001 |
| ES | 2 346 912 | T3 | 10/2010 |
| GB | 822614 | | 10/1959 |
| GB | 1140937 | | 1/1969 |
| GB | 1 399 077 | | 6/1975 |
| GB | 1 443 854 | | 7/1976 |
| GB | 1 472 738 | | 5/1997 |
| WO | 95/10192 | A1 | 4/1995 |

OTHER PUBLICATIONS

Mario Raul Abreu, et al., "Calidad De Las Proteinas Y Evaluacion De Su Ingestion Y De Los Aminoacidos Ensenciales En Un Grupo De Embarazadas", Rev Cubana Aliment Nutr 2000; 14(1):28-32, abstract only.

M. Gandarillas, et al., "Balance de Proteina y Lisina de Origen Animal en la Dieta de Chineno", Cien. Inv. Agr. 31(3): 145-154 2004, abstract only.

http://peruprolife.blogspot.com/2010/11/protilac-materno.html entitled "Protilac Materno 5 veces más proteína de acción inmunológica que la leche materna 30% mayor fijación de calcio". Published on Nov. 12, 2010 with English translation.

http://jonasferreira.eu/archivos/productos/Nutrastart.pdf entitled "Nutrastart®". Published on Jul. 14, 2011 with English translation.

*Primary Examiner* — Brian J Gangle
(74) *Attorney, Agent, or Firm* — Ladas & Parry LLP (57) ABSTRACT

The invention relates to a food supplement having high immunological value, based on a protein matrix, i.e. a food compound with high immunological value, based on the mixture of four protein sources: i. biotechnologically improved bovine colostrum; ii. egg albumin; iii. soy protein isolate; and, iv. concentrated whey protein.

4 Claims, 4 Drawing Sheets

FOOD SUPPLEMENT HAVING HIGH IMMUNOLOGICAL VALUE, BASED ON A PROTEIN MATRIX

RELATED APPLICATION INFORMATION

This application is a 371 of International Application PCT/PE2012/000002 filed 12 Jul. 2012 entitled "Food Supplement Having High Immunological Value, Based On A Protein Matrix", which was published on 17 Jan. 2013, with International Publication Number WO 2013/009194 A1 and which claims priority from Peruvian Patent Application No.: 1340-2011/DIN filed 12 Jul. 2011, the content of which are incorporated herein by reference.

FIELD OF THE ART

The invention relates to a food compound having high immunological value, based on the mixture of four protein sources (i. biotechnologically enhanced bovine colostrum; ii. egg albumin; iii. soy protein isolate; and, iv. whey protein concentrate).

PRIOR ART

Within the spectrum of currently available food supplements there are products that are from different brands and origins, having various qualitative characteristics such as immunostimulatory capacity, high bioavailability (chemical score) and digestibility, but a blend of said characteristics cannot be found in any of them.

EXAMPLES

A search on technological information was conducted based on the elements "soya/leche/huevo/suero" and "soy/milk/egg/whey", resulting in 14 patent applications, obtained from the following information sources:
 European Patent Office Database
 Spanish Patent Office Database
 United States Patent Office Database
 Database of the Directorate for Inventions and New Technologies of Peru The results of said search can be found at the end of this specification as Table 1. In that sense, it can be concluded that the search that was conducted did not find any document similar to a "Food supplement having high immunological value, based on a protein matrix".

The following products based on a single source of proteins, based on any combination thereof or based on a source of proteins combined with bovine colostrum were also found on the market. None of them have the single combination of proteins of the water-soluble bionutritional protein compound of the present invention (BIOPROTEIN+) or a protein base with a biological value of 100%:
 a) TRIFACTOR FORMULA, from 4Life of USA: Capsules and beverages providing transfer factors as support for the immune system.
 b) TRANSFER FACTOR E-XF, from 4Life of USA: Capsules containing bovine colostrum transfer factors combined with egg yolk protein.
 c) NANOFACTOR EXTRA from 4Life of USA: Capsules containing bovine colostrum nanofactor extract.
 d) FORMULA 1, from Herbalife of USA: Nutritional shake containing soy protein isolate, vitamins and minerals.
 e) FORMULA 3, from Herbalife of USA: Protein supplement based on soy protein isolate.
 f) SUPER MIX, from Herbalife of USA: Nutritional shake based on whey protein, soy protein, calcium caseinate, vitamins and minerals.
 g) COLOSTRUM, from Naturavit of USA: Capsules containing bovine colostrum with immune system enhancing properties.
 h) SYNERPROTEIN, from Nature's Sunshine Products of USA: Protein supplement containing soy protein, essential amino acids, vitamins, minerals and fiber.)
 i) COLOSTRUM PLUS, from Nature's Sunshine Products of USA: Capsules containing a combination of colostrum, inositol and herbal elements to nourish and support the immune system.
 j) SUSTAGEN, from Lab. Mead Johnson of USA: Nutritional complement containing milk proteins (whole milk powder), vitamins and minerals.
 k) 80/40 HYPER IMMUNE COLOSTRUM, from Proper Nutrition of USA: Capsules containing bovine colostrum with 40% immunoglobulin G, immune stimulant with a low casein and lactose content.
 l) TRI-MATRIX, from Tegor Sport of Spain: Slowly assimilated combination of whey proteins, egg protein and milk protein (caseinate).
 m) AMINOSTAR WHEY PROTEIN 85%, from Aminostar of Czech Republic: Powder supplement containing whey protein, casein and egg protein complemented with essential amino acids, vitamins and minerals for assimilation during nighttime sleep.
 n) PROTEINA DE SOYA, from Prowinner of Mexico: Powder supplement containing soy protein concentrate complemented with hormonal stimulants (soy isoflavones), with a chemical score of 61%.
 o) INTACT, from Numico Research of Australia: Colostrum powder with a high protein profile.
 p) MIX EGG WHEY PROTEIN, from Mervick Lab of Argentina: Powder supplement containing a combination of whey protein and egg protein, for athletes.
 q) GAINER OVOALBUMEN MIX, from Pulver Suplementos of Argentina: Powder supplement containing a combination of egg protein and whey protein, a muscle mass generator.
 r) Hardcore WHEY GH, from Usn of South Africa: Powder supplement containing a combination of milk protein (caseinate), whey protein, hydrolyzed whey protein collagen, decaffeinated coffee, vitamins and minerals. To strengthen and repair joints for athletes and for favoring growth and weight gain.

DESCRIPTION OF THE INVENTION

When analyzing the currently available food supplements in the preceding section, a group of them ("COLOSTRUM", "TRANSFER FACTORS") that on one hand aims to improve the innate resistance and immunity of healthy people, and on the other hand to help them fight against certain diseases, is identified. Other compounds however aim to provide the organism with quickly assimilated proteins to improve nutrition quality, induce growth and even suitable muscle development in anyone that practices a sport.

The premise for developing an alternative formula is based on the obvious void existing up until now. In reference to immunity, is important to take into account that simply stimulating immune system using different biological agents is insufficient; this stimulation must further be suitably supported by the nutritional status of individual, which an important factor in immune defenses. This is corroborated by the simple fact that the main molecules involved in immune defense (immunoglobulins) are proteins. Therefore, it would be rather useless to stimulate immunity in convalescent people and in people weakened by disease or in chronically malnourished people because the responsiveness of their immune system is weakened.

In the event of this panorama, the water-soluble bionutritional protein compound of the present invention, called "BIOPROTEIN+", is intended for noticeably improving a consumer's immunity, whether in a healthy person or in a person with a disease, because it provides immunoglobulins and transfer factors, which are both immune stimulants, comprised in a bionutritional protein compound carrier that provides nutritional support for the suitable immune system response.

The water-soluble bionutritional protein compound of the present invention, is the result of the combination of biotechnologically enhanced bovine colostrum protein concentrate (with an immunoglobulin concentration five times greater than that of human breast milk and transfer factors), with a protein food having maximum digestibility obtained from three different sources: egg albumin, soy protein isolate and whey protein concentrate.

The steps of the production process of the water-soluble bionutritional protein compound of the present invention are described below:

A. Receiving
   Objective: To receive consumables, packaging material complying with PROLIFE BIOTECH SAC's quality requirements.
   Activities:
   1. Receiving National Consumables: Soy protein isolate, egg albumin powder from temporary warehouse
   2. Receiving Imported Consumables: Whey protein isolate, bovine colostrum protein.
   3. Checking against purchase order.
   4. Quality Control inspection and sampling.
   5. Sent to warehouse destination.

B. Consumables Warehouse
   Objective: To suitably store the consumables that are acquired and those which are temporarily delivered to production such that they do not lose their organoleptic, physicochemical and microbiological characteristics and such that they do not deteriorate.

C. Additives and Packaging Warehouse
   Objective: To suitably store the additives and packaging material that are acquired such that they maintain their organoleptic, physicochemical and/or microbiological characteristics and such that they do not deteriorate.

D. Weighing
   Objective: The consumables comprised in each batch are weighed in this step.
   Activities:
   1. Receiving the consumables of the preceding step.
   2. Weighing the consumables (fractions) according to the formula. (See Table 2 at the end of this specification)
   3. The weighed fractions and sacks are sent to the mixing area, respecting the batch.
   4. Excess consumables are returned to the warehouse foreman at the end of the shift.

E. Mixing
   Objective: Mixing consists of homogenizing all the ingredients according to the formulation. This operation is performed while maintaining an order for the addition of the ingredients.
   Activities:
   1. Emptying the consumables into the area feed hopper connected to the surge bin of the mixer through a screw.
   2. The hopper discharge gate opened to fill the mixer.
   3. After the mixing time, the machine is unloaded using a scow with discharge control.
   4. The feed hopper, surge bin and mixer are all made of stainless steel.

F. Weighing-Packaging (Bulk)
   Objective: Introduce the bulk mixture into sacks all having the same weight.
   Activities:
   1. The mixer content is unloaded into duly coded Kraft paper bags with a polyethylene interior.
   2. Each sack is weighed, then the seal is placed and the bag is sewn shut
   3. The product is removed for temporary storage.

G. Temporary Storage
   Objective: To deliver the finished bulk product to the temporary warehouse for later use
   Activities:
   1. Placing loaded pallets in the temporary warehouse
   2. Identifying each pallet To better understand the process that is performed, the corresponding flow chart is attached at the end of the present specification.

To achieve the highest chemical score and the highest bioavailability (100%), a mathematical model has been used for the combination of the three protein sources. This model, called "linear programming", allowed performing simulations of the combination of different proportions of the protein compounds involved according to their amino acid input (it must be borne in mind that the critical factor for a bioavailability exceeding 99.99% is the limiting amino acid or amino acid having the lowest concentration, which must be complemented by the other sources), until determining the exact proportions that allow perfect amino acid complementation between them.

As a result of applying the "linear programming" model, a water-soluble bionutritional protein compound was obtained consisting of (% by weight):
  a. 6.17% of soy protein isolate;
  b. 76.29% of egg albumin;
  c. 17.04% of whey protein concentrate; and
  d. 0.5% of biotechnologically enhanced bovine colostrum protein concentrate.

CHEMICAL SCORE CERTIFICATE NO. 0607-2008 issued for the water-soluble bionutritional protein compound of the present invention by the Sociedad de Asesoramiento Técnico SAC, attached at the end of the present specification is provided as proof of the optimal amino acid complementation. Said certificate shows that the limiting amino acid is "lysine" with a value above 100%, concluding that "the water-soluble bionutritional protein compound of the present invention exceeds the minimum specification of 99.99% of the Chemical Score".

Another important factor of the water-soluble bionutritional protein compound of the present invention is its presentation as a very tasty shake because the compounds presented in dosage forms (capsules, tablets) are generally the object of misgivings and rejection by average consumers. In contrast, a tasty shake can generate a healthy consumption habit with the aforementioned health benefits.

Bovine Colostrum and Transfer Factors:

Colostrum is the first substance that is secreted by the mammary glands of any mammal, including humans, after giving birth. This process has a very short duration (24 to 96 hours postpartum).

Scientific research conducted in the 1990s has demonstrated that the combination of immune factors and growth factors of bovine colostrum is virtually identical to that of human colostrum, and that bovine colostrum is not "species-specific", i.e., it works effectively in humans as well as in other mammals.

Recent studies have also demonstrated that after going through puberty, the human body gradually produces fewer immune and growth factors, which are important for preventing diseases and for healing damaged tissues in the body. With the loss of these vital components, humans age until they eventually die. Colostrum is the only natural source of these vital components.

The water-soluble bionutritional protein compound of the present invention is an important source of the mentioned immune factors complemented with a protein input as nutritional support, which assures action in the human body.

Transfer Factors:

The immune system is man's best defense against diseases. A disease generally indicates that the immune system has been weakened and failed. This may be due to a poor diet, pollution, chemicals, stress, exposure to electromagnetic radiations, and many other factors that humans must face daily.

Transfer factors are small peptides made up of 40 amino acids which store the entire experience of the immune system. These amino acids work the same way as the twenty-six letters in the alphabet. When they come into contact with a germ, the store the characteristics of that germ in particular, by changing the amino acid sequence.

Transfer factors are the "brains" of the immune system. They are vital for defense against invading diseases and germs. In other words, transfer factors store relevant information for humans in relation to viruses, bacteria, fungi and parasites that have attacked them in the past.

This information is then transferred to certain cells of the immune system, which will defend it against the attack of said viruses, bacteria, fungi and parasites.

Transfer factors also mobilize the so-called natural killer cells and direct them against cancerous cells. Furthermore, certain transfer factor components modulate the immune system to prevent it from attacking the body itself and causing autoimmune diseases such as rheumatoid arthritis, lupus and other illnesses.

Proteins:

Proteins make up about 75% of solids in the body, and they can be structural proteins, enzymes, hormones, oxygen carrier proteins, muscle contraction proteins and others that carry out specific functions inside and outside cells.

In turn, twenty amino acids participate in the protein synthesis in living organisms. Nine of the twenty amino acids are essential amino acids and must be included in the diet; two are semi-essential amino acids (especially during childhood; in adulthood they are relevant in stress and disease) and another nine are non-essential amino acids.

These twenty amino acids are the following:

Essential: Isoleucine, leucine, valine, lysine, methionine, phenylalanine, threonine, tryptophan and histidine.

Semi-essential: Synthesized from essential amino acids. They include tyrosine synthesized phenylalanine, and cysteine synthesized from methionine.

Non-essential: Alanine, arginine, asparagine, glutamic acid, glycine, proline, hydroxyproline and aspartic acid.

Amino acids come from digestion, where they are released from ingested proteins. Free amino acids are then absorbed by means of an active process. Animal proteins have a digestibility of about 100%, and plant proteins have a digestibility of about 70 to 80%.

Biological Value of Proteins:

The biological value is determined by:

The content of essential amino acids

Their digestibility

The use that the human body makes of them

This is important because the quality of a food protein depends on its essential amino acid content. In that regard, the FAO has indicated that a protein is biologically complete when it contains all the essential amino acids in an amount equal to or greater than the amount established for each amino acid in a standard or reference protein.

Amino Acid Score:

Proteins having one or more limiting amino acids, i.e., they are at a smaller proportion than the proportion established in the standard or reference protein, are considered biologically incomplete because they are not used in their entirety. The ratio of the limiting amino acid that is in the smallest proportion with respect to the same amino acid in the reference protein is called the amino acid score (AAS).

Foods of a vegetable origin such as legumes and grains make up a significant percentage of proteins in the diet, but they both have limiting amino acids reducing the efficiency of their use and they must be complemented with others to improve their quality. This can be done by adding small amounts of animal protein to them or by combining them with one another given that legumes are poor in sulfur-containing amino acids (methionine+cystine) and grains such as wheat, rice and corn, are poor in lysine (corn is also poor in tryptophan and rice is poor in threonine). Since the limiting amino acids of legumes and grains are different, a mixture of both will allow improving the amino acid score and thereby the biological quality of the protein of the mixture, a process which is called amino acid complementation.

Diet Quality:

The FAO and WHO have stressed the importance of measuring the quality of proteins in the diet (amino acids score—AAS—, digestibility) and the importance of consuming biologically complete proteins because they are factors related to diet quality and should be taken into consideration when designing a diet with a certain amount of proteins for the population (1,2). When these factors are suitably handled in the dally diet, they must assure for the consumer 100% labile body protein restoration and thus allow 100% body cell regeneration.

In the case of not having experimental data concerning digestibility of the protein in the diet or of the protein sources that make it up, it is advisable to use a digestibility value of 85% for those diets consisting mainly of plant foods and of 95% for those which are made up of a high percentage of refined grains and foods from an animal origin. However, in the first case there is a 15% deficiency and in the second case a 5% deficiency, and this gap causes greater body cell deterioration.

Technical Problems being Solved:

1. Supply of transfer factors and immunoglobulins in the daily diet. Human beings are best immunized during the breastfeeding stage first given the input of colostrum transfer factors and then immunoglobulins, from breast milk. When breastfeeding ends, the supply of such important immune factors, which will not be recovered again, also ends. Bioprotein+ is a food alternative that again allows access to such important nutrients in the form of a shake to be consumed daily.
2. 100% labile body protein recovery (100% cell regeneration). To date, in order to achieve an amino acid input and a biological value close to the daily protein requirements of human nutrition, the only alternative was to combine different protein sources, without this entailing a 100% recovery, i.e., total cell regeneration.

In practice, this also represents other additional limitations for the average consumer, such as unawareness of the most suitable types of foods to be combined or the exact proportions thereof for their effective amino acid complementation.

In the water-soluble bionutritional protein compound of the present invention, the protein sources: i. biologically enhanced bovine colostrum protein concentrate; ii. egg albumin; iii. soy protein isolate; and, iv. whey protein concentrate, have been combined in proportions such that they provide 100% bioavailability, i.e., they assure for the organism 100% labile body protein recovery and thereby allows 100% body cell regeneration.

The water-soluble bionutritional protein compound of the present invention is a bionutritional food having immunological and nutraceutical capabilities that are unmatched worldwide.

REFERENCES

1. Calidad de las proteínas y Evaluación de su Ingestión y de los Aminoácidos Esenciales en un Grupo de Embarazadas. Rev Cubana Aliment Nutr 2000; 14(1):28-32.
2. Balance de la Proteína y Lisina de Origen Animal en la dicta del Chileno. Cien. Inv. Agr. 31(3): 145-154.2004.

Fields of Application of a Food Supplement Having High Immunological Value, Based on a Protein Matrix Water-Soluble Bionutritional Protein Compound of the Present Invention) in Human Nutrition:

Colostrum is the first liquid produced by a mother's mammary glands within the first 24-48 hours after a baby is born. Colostrum, provides immune and growth factors essential for life that assure the newborn's health and vitality. Colostrum is so important that most babies born to any animal would die if they could not take it.

After puberty, the body slowly begins to reduce its production of the growth hormone, necessary for the reproduction of virtually all the cells and tissues in the body. It has been demonstrated that at 80 years of age, the body produces virtually no growth hormone, and therefore, from that moment on humans age quickly and die. In fact, colostrum growth factors are the hormones that stimulate normal reproduction of cell tissue. The normal reproduction of cells means slow aging and the prevention of cancer, wrinkles and general weakness.

Several years ago, The New England Journal of Medicine expressed that supplementing growth hormones to their most suitable levels could slow down the processes of aging and possibly stop them.

Food Supplement Having High Immunological Value (Water-Soluble Bionutritional Protein Compound of the Present Invention) in Disease Prevention The onset of almost all diseases, whether they are infectious or degenerative, including cancer and heart diseases, is preceded or accompanied by a decrease in immune system functions. Studies demonstrate that colostrum contains powerful factors (immunoglobulins, lactoferrin, cytokines and interferon) that boost the immune reaction. This is another advantage of water-soluble bionutritional protein compound of the present invention from ProLife. The colostrum used in its formulation has an immunoglobulin (IgG) content that is five times greater than that of human colostrum.

Colostrum also contains PRP (Proline-rich Peptides) which according to medical studies aid in strengthening a hypoactive immune system, particularly when it has 100% bioavailability. PRPs help the thymus restore its optimal operating capacity. This gland produces T-cells that fight against viruses and antigens. The PRPs found in colostrum also help stabilize hyperactive immune system in autoimmune diseases. This makes colostrum extremely effective against diseases such as chronic fatigue syndrome, fibromyalgia, multiple sclerosis, rheumatoid arthritis, lupus and scleroderma.

Food Supplement Having High Immunological Value (Water-Soluble Bionutritional Protein Compound of the Present Invention) in Increasing Muscle Mass and Controlling Body Weight.

According to various serious publications on bodybuilding colostrum is extremely potent in generating muscle mass when it is accompanied by suitable exercises.

Research has demonstrated that humans readily assimilate bovine colostrum, particularly if said bovine colostrum has a suitable chemical score. It is also known that only bovine colostrum contains glycoproteins and protease inhibitors which are extremely effective in protecting the active components of colostrum against the destructive effect of digestive enzymes and stomach acids of an adult human.

According to Dr. Robert Preston of the US National Institute on Nutrition Research, "colostrum is so innocuous that it has been made by nature as the first food for newborns. It would be difficult to imagine a more natural or beneficial substance".

Food Supplement Having High Immunological Value (Bioprotein+) in Intestinal Permeability Intestinal permeability (leaky gut syndrome) and irritable bowel syndrome occur primarily because the bowel has been exposed to infectious agents such as bacteria, viruses, fungi (candidiasis), parasites and various toxins. There are other causes as well, including a poor diet, drinking alcoholic beverages, anti-inflammatory drugs, cytotoxic drugs and body stress reactions to situations such as heart attacks, surgeries and any other form of shock.

This condition can lead to multiple problems which are very frequent, such as diarrhea, poor assimilation of food, as well as food allergies. It is also often associated with more serious illnesses, such as Crohn's Disease. Intestinal symptoms of this type are furthermore often a component of many serious autoimmune diseases such as muscular dystrophy, fibromyalgia and scleroderma. In fact, many doctors believe that most diseases originate in the bowel.

The studies demonstrate that colostrum can stop leaky gut syndrome, with its unique combination of immune and growth factors that seem to have been custom designed by nature as a remedy for this disease, Immunoglobulins (IgA, IgG and IgM), lactoferrin and other immune factors can inhibit the reproduction of invading pathogens (infections) and protect against toxins. The epithelial growth factor of colostrum stimulates the reparation of intestinal membranes at the cellular level. The anti-inflammatory action it provokes reduces cell spacing, thereby reducing hyperpermeability.

Given that the bovine colostrum of water-soluble bionutritional protein compound of the present invention reduces intestinal permeability and its high bioavailability greatly increases its assimilation, it also increases the efficacy of all other nutrients normally consumed in the diet.

Food Supplement Having High Immunological Value (Water-Soluble Bionutritional Protein Compound of the Present Invention) in Arthritis and Autoimmune Response.

Arthritis is almost always accompanied by inflammation. Inflammation and the pain that accompanies it are, in fact, a mild form of disease or of a deficient autoimmune operation. It is the result of the attack started by the Immune system against antigens after this response is no longer needed. Many much more serious autoimmune diseases, such as muscular dystrophy (Lou Gehrig's disease) and scleroderma also derive from a hyperactive immune system.

Recent studies have demonstrated that natural compounds containing sulfur, such as glucosamine sulfate, have a beneficial effect on inflammation, especially inflammation caused by arthritis. Colostrum is an excellent source of these micronutrients containing sulfur, including "MSM", or methylsulfonylmethane, which has also garnered a great deal of international attention as of late. In fact, colostrum is one of the sources richest in MSMs known today. It also has other powerful components, including two of the strongest anti-inflammatory components. This gives it a great deal more of anti-inflammatory strength than sulfur-containing components alone.

Effects of 100% Bioavailable Colostrum (Water-Soluble Bionutritional Protein Compound of the Present Invention) in Osteoporosis Studies demonstrate that the transforming growth factor) (TgF) contained in colostrum can help prevent osteoporosis.

Osteoclasts are cells that dissolve bone, undermining is structure and causing porosity and loss of bone strength which is called osteoporosis. In turn, osteoblasts are the cells that build bone. As one ages, the number of osteoblasts drops and the number of osteoclasts increases. This is especially true in postmenopausal women because it has been demonstrated that a drop in estrogen levels causes an increase in the number of osteoclasts.

A study in Natural Medicine demonstrates that TgF-B factor which is naturally found in colostrum alone is also produced naturally by osteoblasts. The study also demonstrates that TgF-B dramatically increases cell apoptosis (cell death) among osteoclasts. The study indicates that TgF-B could reduce the risk of this disease.

Food Supplement Having High Immunological Value (Water-Soluble Bionutritional Protein Compound of the Present Invention) in Muscle Development According to clinical studies, colostrum may be the most potent natural substance that has been discovered to help athletes obtain desired results.

In fact, many bodybuilders and professional trainers say that colostrum is the most effective muscle development agent they have ever used.

In his article in Ironman (certified and specialized bodybuilding magazine), Daniel Shawn states that IgG-1 (insulin-like growth factor) in colostrum "has a greater anabolic effect than any known compound, including steroids".

IgG-1 factor can "promote muscle growth by itself", Steve Schwade, assistant editor of Muscle & Fitness, writes in his issue from May 1992. "Bovine colostrum has an IgG-1 concentration that is higher than human colostrum", he continues, "and its structure is virtually identical. Human IgG-1 and bovine IgG-1 differ only in three of the 67 amino acids making up the molecule of this factor. Because of that similarity, bovine IgG-1 is as potent as human IgG-1."

Mr. Schwade continues to mention current studies that have demonstrated that colostrum makes proteins break down more slowly and " . . . stimulates the transport of glucose in to the muscle", which means that muscles can more efficiently use the nutritive substances that are available to it.

Food Supplement Having High Immunological Value (Water-Soluble Bionutritional Protein Compound of the Present Invention) in Weight Control.

With respect to fat metabolism, colostrum growth factors "cause a switch from using carbohydrates to using fat. This does not mean that one can take in more fat, but it does mean that the body can burn more of it, including the fat that the body manufactures from carbohydrates and proteins that one eats, and therefore more efficiently produce fuel for cells", Mr. Schwade remarks.

In conclusion, he stated: "In summary, growth factors (in colostrum) speed up protein synthesis and slow down protein catabolism (breaking down proteins), which leads to an increase in lean muscle mass without the corresponding increase in adipose tissue".

And once again, Daniel Shawn of Ironman, states: "Quite simply, IgG-1 factor is the ultimate growth factor made up of anabolic peptides".

Food Supplement Having High Value (Water-Soluble Bionutritional Protein Compound of the Present Invention) in Sports More studies have recently been conducted with athletes. In his article in Nutrition Science News in May 1996, Dr. Edmund Burke reports on research conducted with the Finish Olympic Ski Team. "The athletes trained very hard and their creatine kinase levels were analyzed every seven days. Creatine kinase is an extremely important muscle enzyme that has been proven to be a signal of damage in muscle cells which is detected in the blood. Therefore, when creatine levels increase, it is often indicative of significant muscle damage. Compared with the members the team that took placebos, the athletes who drank a beverage made with colostrum experienced approximately only if the increase in creatine kinase levels four days after having performed tiring exercises". In the subjective aspect, the athletes also said that the felt less tired and that their performance seemed to nave improved.

In that same article, Burke continues to say tint colostrum also "improves athletic performance through the bowel". Colostrum increases the assimilation of nutrients through these and thereby improves the efficiency of the absorption of carbohydrates and amino acids. Growth factors containing colostrum also "seal" the digestive pathways and protect them against ulcers, which would reduce the efficiency of absorption.

Therefore, when one takes colostrum, more nutrients from food can be used as fuel for exercise whether the exercise is cardiovascular or a bodybuilding exercise.

Figure 1:
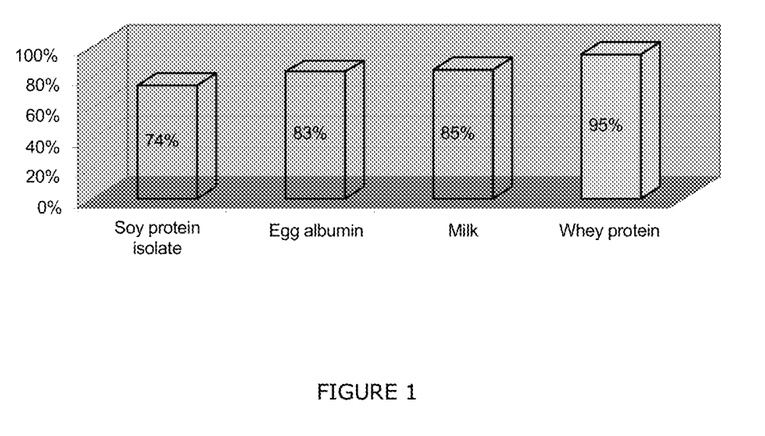
FIG. 1 shows a comparative graph of the biological value of proteins frequently used in human food.
Figure 2:
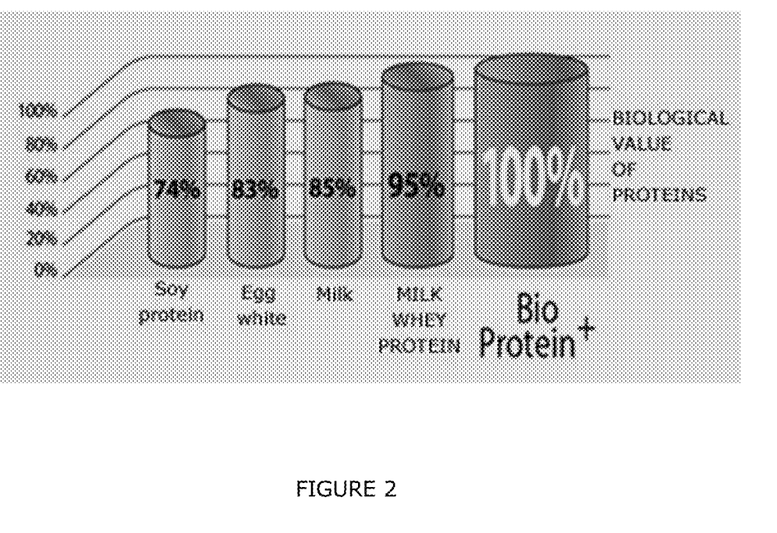
FIG. 2 shows a comparative graph of the biological value of the water-soluble bionutritional protein compound of the present invention versus other proteins frequently used in human food.

Inventive Step:

As mentioned in the specification, proteins naturally have a significant limitation in their biological value (BV). According to the FAO, whey protein has the highest BV: 95% (FIG. 1).

On the other hand, even though colostrum has a very complete amino acid profile and proven positive effects on health, it does not reach 100% bioavailability either.

The permanent concern among doctors, nutritionists and other health professionals has been to find or formulate a protein compound of a natural origin which, when administered parenterally, allows protein metabolism in the organism which assures 100% labile body protein restoration and thus allows 100% cell regeneration in the human organism. If a health promoting effect is considered together with the foregoing, a functional food having nutraceutical capabilities that are unmatched worldwide would be obtained.

Figure 3:
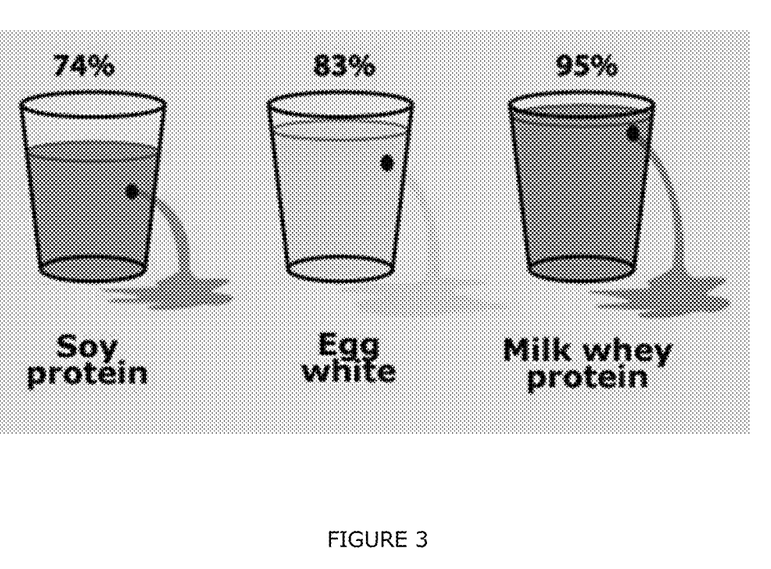
FIG. 3 shows a graphical representation of different protein sources and their limiting amino acids.

To show this point, FIG. 3 depicts various protein sources as a glass and their limiting amino acid as a hole; their respective biological values, BVs, are also shown. If they all had the capability of being filled to the brim, cell regeneration would be 100%, i.e., 100% bioavailability. The "limiting amino acid" causes that protein to lose the capability of being filled to the brim and reaching 100% bioavailability.

Figure 4:
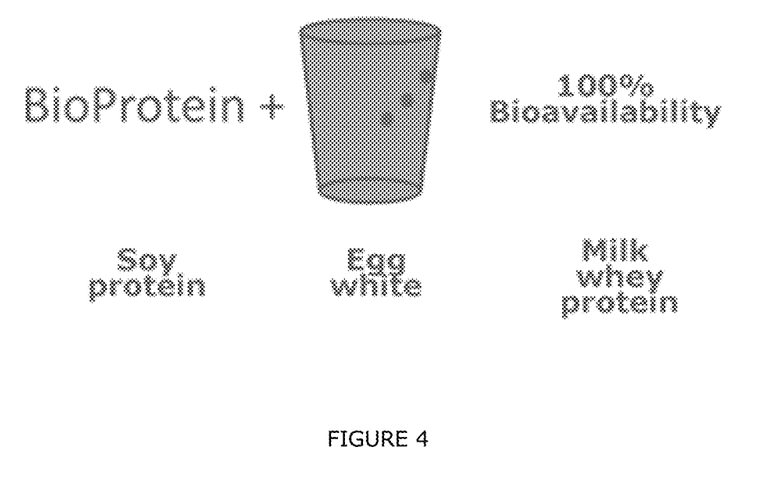
FIG. 4 shows a graphical representation of the amino acid complementation of different protein sources.

The starting point of the present invention is based on the assumption that by combining different protein sources, the limiting amino acid of one source could be provided by another source in a sufficient amount. FIG. 4 shows a graphical representation of said premise as if the four glasses were placed. together. Each glass would cover the hole of another glass such that there would no longer be "leaks" and the limiting amino acid would reach a 100% chemical score (bioavailability).

According to the medical evidence available, colostrum with a 100% chemical score can provide the human organism with the following benefits:

Regenerate and speed up the normal growth of muscle tissues, bones, cartilage, collagen in the skin and nervous tissues.

Help burn fat by using it as a fuel instead of using muscle tissue while fasting (and in a dietary regimen).

Help develop and maintain lean muscle tissue.

Repair the body's genetic material: DNA and RNA.

Stabilize and regulate blood sugar levels.

Control infection and pain associated with gingivitis, sensitive teeth and dental procedures.

Help regulate blood glucose levels and the chemical substances in the brain that keep people alert and facilitate concentration.

Help regulate chemical substances that give people a feeling of well-being and heighten one's mood.

TABLE 1

| Source of Information | Country | Name | Number | Similar Components | Description |
|---|---|---|---|---|---|
| Patent applications published by the US Office | United States | High protein dough mix | U.S. Pat. No. 5,320,859 | Products of soy, milk, egg and whey | Dough used for baking and serving as cookies, cakes, brownies, etc. |
| | United States | Controlled-viscosity food flavoring system | U.S. 2003/0044503 | Egg (white), skim milk, milk protein concentrate, whey protein concentrate and partially hydrogenated soybean oil | Flavoring or seasoning for foods |
| | United States | Contextured semimoist meat analogs | U.S. Pat. No. 4,132,809 | Soy proteins, whey solids, milk solids and egg solids. | Meat substitute with a flavor and nutrients very similar to natural meat |
| | United States | Process for fibered meat analogs | U.S. Pat. No. 4,021,584 | Purified soy whites, milk powder and whey | Preparation of large pieces and strips of texturized protein material |
| Patent applications published by the European Office | Canada | High protein aerated food composition | CA 2552 313 | Egg white, white egg, soy protein derivatives, milk compound derivatives, milk proteins, whey proteins and soybean oil. | Related to the aerated food composition and the method for creating it. |
| | Canada | Probiotic compounds derived from *Lactobacillus Casei* Strain KE01 | CA 2 520 178 | Soy protein, egg white, milk proteins and soybean oil | Used in animals for pathogenic diseases and for maintaining animal health. |
| | Great Britain | High protein mixture for use in bakery products | GB 1 472 738 | Whey protein concentrate, lactalbumin, egg white, milk solids and whey. | Mixture used for baking bakery products so that they contain a high percentage of proteins and thus have a high biological value. Particularly intended for preparing bread. |
| | Great Britain | Nut-like texturized | GB 1399 077 | Skim milk solids, soy | |

TABLE 1-continued

| Source of Information | Country | Name | Number | Similar Components | Description |
|---|---|---|---|---|---|
| | | food composition | | protein, egg white and dry whey. | |
| | Great Britain | Shake composition and preparation | GB 1 140 937 | Milk, skim milk solids, whey solids, soy protein and egg white | Powder whipped cream. |
| | Great Britain | Fat composition and preparation | GB 822 614 | Skim milk powder, whey, soy protein derivatives, egg white and yolk. | Flavoring for preparing butter, mayonnaise, dressings, etc. |
| | Great Britain | Refrigerated cookie dough | GB 1443 854 | Skim milk powder, whey solids, egg white and soy | Preparation of cookies |
| Patent applications published by the Japanese Office | Japan | Composition to reduce fluctuations of the plasma concentration of natural amino acids and use thereof | JP 07 278009 | Whey protein concentrate, purified milk protein, white egg and soybean | To obtain a food composition capable of neutralizing amino acids. |
| | Japan | Nutrient composition high in conservatives, stability and palatability | JP 07 2555398 | Milk casein, whey protein, soy protein and chicken egg protein. | To obtain nutrients containing enzymes that break down wheat germ. |
| | Japan | Foamy emulsified oil and fat composition | JP 10 088184 | Soybean oil, milk protein, whey protein and chicken egg | Obtain higher volumes in cakes. |

35

TABLE 2

LIST OF INGREDIENTS: BIOPROTEIN+

| CONSUMABLE | ORIGIN | Percentage range of participation by weight |
|---|---|---|
| Soy protein isolate | National | 35-45% |
| Egg albumin protein | National | 75-85% |
| Whey protein isolate (IWPC) | Imported (Glanbia Nutritionals) | 15-25% |
| Bovine colostrum protein (50% IgG) | Imported (Glanbia Nutritionals) | 0.1-5.0% |

Sociedad de Asesoramiento Técnico S.A.C.

CHEMICAL SCORE CERTIFICATE NO. 0607-2008
(CERTICATION SYSTEM No. 1)

1.- APPLICANT'S INFORMATION
   APPLICANT'S NAME : PROLIFE BIOTEC S.A.C.
   ADDRESS : Calle Camino Real No. 1801- Int. D-2- Santiago de Surco- Lima
   CERTIFICATION SYSTEM : No. 1 (Type or Prototype)

2.- PRODUCT INFORMATION
   PRODUCT : BIOPROTEIN
   BRAND : NO BRAND
   CONTAINER : Non-lithographed polyethylene bag x 500g
   PRODUCER'S NAME : BIOPROTEIN 3.- REFERENCE DOCUMENTS FOR CERTIFICATION
   Technical specifications provided by Client.
   Minimum 99.99% Chemical Score 4.- TESTING METHODS : NUTRITIONAL NEEDS AND DIET QUALITY SELF-INSTRUCTION MANUAL SONIA OLIVARES *et al.* UNIVERSIDAD DE CHILE. INTA 1994

5.- RESULTS : According to Test Report No. 004-2008

| AMINO ACID | % |
|---|---|
| HISTIDINE | 126.53 |
| ISOLEUCINE | 192.2 |
| LEUCINE | 132.47 |
| LYSINE | 111.87 |
| MET+CYS | 152.27 |
| PHEN+TYR | 123.2 |
| THREONINE | 141.66 |
| TRYPTOPHAN | 133.01 |
| VALINE | 139.34 |
| LIMITING AMINO ACID | |
| LYSINE | 111.87 |

6.- CONCLUSIONS
   According to the theoretical calculation, the Limiting Amino Acid, LYSINE, of the Product BIOPROTEIN exceeds the minimum specification of 99.99% of the Chemical Score.

Lima, April 1, 2008                                 Evaluated by Bach Verónica Benites S.
RG/.

[illegible signature]     [Stamp]
FIDEL POMA M., ENG.
HEAD OF CERTIFICATION DIVISION
ENGINEERING ASSOCIATION MEMBER NO. 19392

CERTIFICATION ISSUED ON THE BASIS OF THE RESULTS OBTAINED IN OUR LABORATORY. THE VALIDITY OF THE PRESENT CERTIFICATE IS FOR 3 MONTHS AFTER THE ISSUE DATE. APPLICABLE ONLY FOR THE SAMPLE PROVIDED BY THE CLIENT. COMPLETE AND/OR PARTIAL REPRODUCTION OF THE PRESENT CERTIFICATE IS FORBIDDEN. PHOTOCOPY IS NOT VALID. CONFIRMATION SAMPLES OF THESE PRODUCTS ARE STORED FOR 3 MONTHS AFTER THE ISSUE DATE.

The invention claimed is:

1. A water-soluble bionutritional protein compound, comprising the following % by weight:
   a) about 6.17% of soy protein isolate;
   b) about 76.29% of egg albumin;
   c) about 17.04% of whey protein concentrate; and
   d) about 0.5% of bovine colostrum protein concentrate.

2. A water-soluble bionutritional protein compound, consisting of the following % by weight:
   a) 6.17% of soy protein isolate;
   b) 76.29% of egg albumin;
   c) 17.04% of whey protein concentrate; and
   d) 0.5% of bovine colostrum protein concentrate.

3. A water-soluble bionutritional protein compound according to claim 1 wherein said bovine colostrum protein concentrate contains at least 50% IgG, by weight.

4. A water-soluble bionutritional protein compound according to claim 2 wherein said bovine colostrum protein concentrate contains at least 50% IgG, by weight.

* * * * *